United States Patent [19]

Hill

[11] Patent Number: 4,562,278

[45] Date of Patent: Dec. 31, 1985

[54] ORGANOSILICON COMPOUNDS AND PREPARATION AND USE THEREOF

[75] Inventor: Michael P. Hill, Saint Lythans, Wales

[73] Assignee: Dow Corning, Ltd., Barry, Wales

[21] Appl. No.: 660,160

[22] Filed: Oct. 12, 1984

[51] Int. Cl.$^4$ .......................... C07F 7/08; C07F 7/10; C07F 7/18

[52] U.S. Cl. .................................. 556/418; 556/440; 424/59

[58] Field of Search ................... 556/418, 440; 424/59

[56] References Cited

U.S. PATENT DOCUMENTS

| | | | |
|---|---|---|---|
| 3,513,184 | 5/1970 | Brison et al. | 556/418 |
| 3,853,935 | 12/1974 | Roshdy et al. | 556/418 |
| 4,472,590 | 9/1984 | Mitchell | 556/418 |

FOREIGN PATENT DOCUMENTS

| | | | |
|---|---|---|---|
| 2215629 | 10/1973 | Fed. Rep. of Germany | 556/418 |
| 1164522 | 9/1969 | United Kingdom . | |
| 1373458 | 11/1974 | United Kingdom . | |
| 2030581 | 4/1980 | United Kingdom | 556/440 |

*Primary Examiner*—Paul F. Shaver

*Attorney, Agent, or Firm*—George A. Grindahl

[57] ABSTRACT

Organosilicon compounds which are silanes or siloxanes characterized by the presence of silicon-bonded groups of the formula

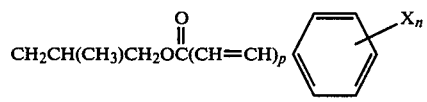

in which X represents —OH, —OCH$_3$ or OC$_2$H$_5$ when p=1 or —OH or dialkylamino when p=0, n can be 0 or 1 and p=0 or 1.

The compounds are prepared by the reaction of a silane or siloxane containing silicon-bonded hydrogen with a compound

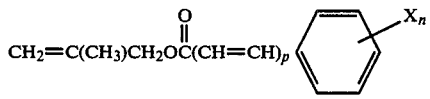

9 Claims, No Drawings

ORGANOSILICON COMPOUNDS AND PREPARATION AND USE THEREOF

This invention relates to novel organosilicon compounds which absorb ultra violet radiation and which are useful inter alia as sunscreen agents.

A number of organic compounds, generally organic acids and derivatives thereof, are known to have U.V.-absorbing properties and are employed on a commercial scale as ingredients in sunscreen preparations. Although such materials function adequately they are easily removed from the substrate to which they have been applied. For example, cosmetic sunscreen preparations can be removed during bathing thus requiring repeated applications if protection is to be maintained. It is also desirable that the active ingredient remain on the surface of the skin rather than be absorbed thereby.

British Pat. No. 1 164 522 discloses organosilicon compounds which are useful as sunscreen agents and which may be prepared by the reaction of an organosilicon compound having at least one SiH linkage with an organic compound having terminal unsaturation. According to Pat. No. 1 164 522 allyl cinnamate is particularly preferred as the unsaturated organic compound. The use of allyl cinnamate for the preparation of such compounds has, however, been found to be less than satisfactory. Due to the occurrence of secondary rearrangement reactions the yield of the desired product is generally poor.

A method of preparing organosilicon cinnamates which avoids such secondary reactions is described in British Pat. No. 1 373 458. The said method involves the reaction of allyl cinnamate with a silane or siloxane having silicon-bonded mercaptoalkyl groups. Usually, however, some residual odour of the mercaptoalkyl reactant remains in the product thus rendering it generally unsuitable for cosmetic applications.

According to this invention there are provided organosilicon compounds which are
(1) silanes represented by the general formula

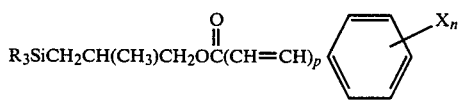

or (2) siloxanes having at least one unit represented by the general formula

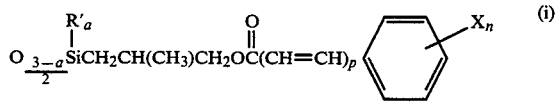

any other units present in the said siloxanes being those represented by the general formula

wherein each R represents a halogen atom, an alkyl group having from 1 to 4 carbon atoms or a phenyl group, an alkoxy group having less than 8 carbon atoms or an alkoxyalkoxy group having less than 8 carbon atoms, R' represents an alkoxy group having less than 8 carbon atoms, an alkoxyalkoxy group having less than 8 carbon atoms, a methyl group or a phenyl group, X represents a hydroxy group, methoxy group or ethoxy group when p=1 or a hydroxy group or —NQ$_2$ group, in which each Q is lower alkyl, when p=0, Z represents a hydrogen atom, a monovalent hydrocarbon group or a monovalent halogenated hydrocarbon group, a is 0, 1 or 2, b is 0, 1, 2 or 3, n is 0 or 1 and p is 0 or 1.

In the general formulae of the silanes and siloxanes of this invention each R may be for example chlorine, bromine, methyl, ethyl, methoxy, ethoxy or methoxyethoxy, and X, when present, represents —OH or the methoxy group. The R' substituents may each be methyl, phenyl or an alkoxy or alkoxyalkoxy group having less than 8 carbon atoms e.g. methoxy, ethoxy or methoxyethoxy. Each of the Z substituents may be H, or a monovalent hydrocarbon or halogenated hydrocarbon group, preferably having less than 8 carbon atoms, for example methyl, vinyl, phenyl or 3,3,3-trifluoropropyl. In the group —NQ$_2$ each Q may be alkyl group having from 1 to about 4 atoms. Preferably Q is methyl or ethyl.

The siloxanes of this invention have in the molecule at least one unit falling within the general formula (i). They may be homopolymers consisting only of such units (i) or they may be copolymers containing both units (i) and units falling within the general formula (ii). The siloxanes may vary in molecular size from the disiloxanes to high molecular weight homopolymers and copolymers and may range in consistency from freely flowing liquids to gum-like or resinous solids. Preferred, at least for cosmetic applications, are the liquid, substantially linear siloxane homopolymers and copolymers. It is also preferred for such applications that at least 30 percent and preferably at least 70 percent of the R' and Z substituents are methyl groups.

It has been found that compounds wherein X represents methoxy, ethoxy or —NX$_2$ e.g. dimethylamino, exhibit high absorbance in the erythemic region (290-320 nm.). Such compounds are therefore preferred for use in applications e.g. cosmetic sunscreen products where absorption in this region of the UV spectrum is desired.

The silanes and siloxanes of this invention can be prepared by the reaction of a silane or siloxane having SiH groups with methallylcinnamate, methallylmethoxycinnamate, methallylhydroxycinnamate, methallyl salicylate or a methallyl ester of an N,N-dialkylaminobenzoic acid. This invention therefore also includes a process for the preparation of organosilicon compounds of the kind specified herein which comprises reacting together (A) a compound of the general formula

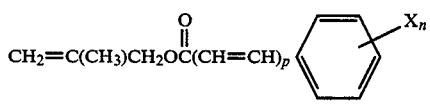

wherein X represents —OH, —OCH$_3$ or —OC$_2$H$_5$ when p is 1, or —OH or —NQ$_2$ when p=0, p is 0 or 1 and n is 0 or 1, and (B) an organosilicon compound which is a silane of the general formula R$_3$SiH or a siloxane having in the molecule at least one unit of the general formula

any other units present in the siloxane being those represented by the general formula

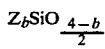

wherein R', Z, a and b are as hereinbefore defined.

The reaction between (A) and (B) may be carried out employing known procedures for the addition of silicon-bonded hydrogen atoms to groups containing olefinic unsaturation. Thus, such reactions are generally catalysed by a platinum group metal or a compound or complex of such a metal. Examples of catalysts which may be employed in the reaction between (A) and (B) are platinum on carbon, chloroplatinic acid, platinum acetyl acetonate, complexes of platinum compounds with unsaturated compounds e.g. olefins and vinyl siloxanes, complexes of rhodium and palladium compounds and complexes of platinum compounds supported on inorganic substrates. The addition reaction may be performed at sub-atmospheric, atmospheric or super-atmospheric pressure and in the presence or absence of solvents. It is generally preferred to employ a solvent e.g. toluene or xylene in the reaction mixture. It is also preferred to use elevated reaction temperatures e.g. from about 50° C. up to the reflux temperature of the reaction mixture. Preferably stoichiometric proportions of (A) and (B) are employed or a slight stoichiometric excess of (A). However, a stoichiometric deficiency of (A) can be employed if residual silicon-bonded hydrogen is desired in the product.

Siloxanes of the invention can also be prepared from the corresponding hydrolysable silanes by hydrolysis or cohydrolysis or by equilibration of the silanes with cyclic or linear siloxanes.

The silanes and siloxanes of this invention absorb ultra-violet radiation and are therefore useful as agents for preventing sunburn. They may be applied per se to the skin but are more preferably formulated into compositions with, for example, inert carriers e.g. solvents such as ethanol, isopropanol, glycerine and mineral oil and cream base materials such as stearic acid, propylene glycol, beeswax and cetyl alcohol. Other conventional ingredients e.g. perfumes and known U.V. absorbing substances may also be included in the formulated compositions. The silanes and siloxanes of the invention are also useful in the coating of substrates, e.g. wood, plastics or metal, to which they may be applied either per se or as additives to coating compositions.

The following examples in which Me represents the methyl group illustrate the invention.

EXAMPLE 1

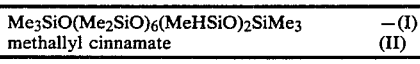
| Me₃SiO(Me₂SiO)₆(MeHSiO)₂SiMe₃ | —(I) |
| methallyl cinnamate | (II) |

Toluene (14 g) and a platinum catalyst (0.49 g) were charged to a flask and then heated to 103° C., the platinum catalyst being obtained from the reaction of a methylvinylsiloxane oligomer and chloroplatinic acid.

Reactant I (52.8 g) and reactant II (30 g) were dissolved in toluene (46 g) and the solution added slowly via a dropping funnel to the contents of the flask. The temperature of the flask was maintained at approximately 100° C. during the addition and for 18 hours after addition had been completed. The toluene was then removed by distillation under vacuum to leave a polymer having a viscosity of 100 cS at 25° C. and the average formula

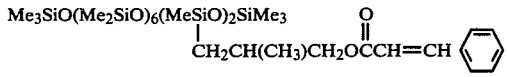

After washing three times with methanol the polymer contained less than 1% by weight of methallyl cinnamate.

The wavelength of maximum absorbtion for the polymer λmax was 277 nm.

EXAMPLE 2

| Me₃SiO(Me₂SiO)₆(MeHSiO)₂SiMe₃ | (I) |
| methallyl p-methoxy cinnamate | (II) |

The platinum catalyst described in Example I (0.6 g) was dissolved in toluene (7.3 g) and the solution charged to a flask fitted with a condenser and dropping funnel. The contents of the flask were then heated to 100° C. and a mixture of reactant I (64 g), reactant II (46 g) and toluene (65 g) added slowly from the dropping funnel. After 20 hours a second portion (0.6 g) of the platinum catalyst was added and the reaction mixture maintained at about 100° C. for a further 6 hours.

Toluene was removed from the reaction mixture by vacuum distillation and the remaining polymer washed twice with aqueous methanol solution. The product was a clear polymer of the average formula

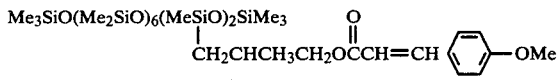

essentially free of II and having a viscosity of 220 cS at 25° C. The wavelength of maximum absorbtion for the polymer λmax was 308 nm.

The methallyl p-methoxycinnamate employed as reactant in this Example was prepared as follows.

712.8 g (4 moles) p-methoxy cinnamic acid were charged to a 6 l flask fitted with stirrer, thermometer, condenser and dropping funnel, and dissolved in 1200 ml N,N-dimethyl formamide at 70° C. To this solution 728.6 g triethylamine (7.2 moles) and 579.5 g (6.4 moles) methallylchloride were added successively. The reaction mixture was maintained overnight at 65°–73° C., then poured on ice, and extracted with dichloromethane. The organic layer was washed twice with 1N sodium hydroxide, then with water and dried over sodium sulphate. After distilling off the solvent the residue was dissolved in 4 l boiling pentane. After cooling at +10° C. a total of 878.4 g crystals (m.p. 42°–43° C.) were obtained in two crops which were recrystallized from 5 l pentane, giving 779.1 g (83.9% yield) white crystals of m.p. 43°–43.5° C.

EXAMPLE 3

0.325 g (0.1×10⁻⁴ moles Pt) of a complex of chloroplatinic acid and a low molecular weight methylvinylsiloxane was dissolved in 6.6 g analytical purity toluene and charged to a flask fitted with a condenser, agitator and dropping funnel. This was then heated to about 90° C. and to the heated mixture was added a solution containing 37.1 g of the methylhydrogensiloxane reactant of Example 1, 19.2 g of salicylic acid and 50 g of analytical purity toluene. The flask temperature was raised to reflux temperature (115° C.) during addition and maintained there for 3 hours.

The solvent was then removed by vacuum distillation and the residue allowed to cool. After filtration there was obtained 53.3 g of a straw-coloured, slightly hazy liquid having the following properties:

| | |
|---|---|
| Viscosity (25° C.) | 53.8 cP |
| λ max | 305 nm |
| Extinction coefficient (Molar) | 3475 |
| Extinction coefficient (1% in CH$_2$Cl$_2$) | 61.6 |

EXAMPLE 4

Employing the procedure described in Example 3 37.1 g of the same siloxane reactant was reacted with 21.9 g N,N-dimethylamino benzoic acid methallyl ester. The reflux period employed in this experiment was extended to 17 hours. After removal of the toluene by vacuum distillation the residue was allowed to cool and was filtered. There was obtained 51.8 g of a hazy, straw coloured liquid having some residual silicon-bonded hydrogen and the following properties:

| | |
|---|---|
| Viscosity (25° C.) | 189 cP |
| λ max | 310 nm |
| Extinction Coefficient (Molar) | 28760 |
| Extinction Coefficient (1% CH$_2$)Cl$_2$) | 487 |

That which is claimed is:

1. Organosilicon compounds selected from
(1) silanes represented by the general formula

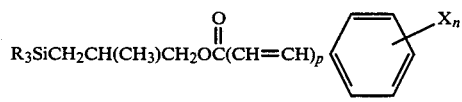

or
(2) siloxanes having at least one unit represented by the general formula

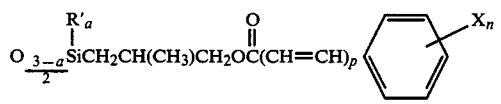 (i)

any other units present in the said siloxanes being those represented by the general formula

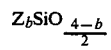 (ii)

in which general formulae R represents a halogen atom, an alkyl group having from 1 to 4 carbon atoms or a phenyl group, an alkoxy group having less than 8 carbon atoms or an alkoxyalkoxy group having less than 8 carbon atoms, R' represents an alkoxy group having less than 8 carbon atoms, a methyl group or a phenyl group, X represents a hydroxyl group, methoxy group or ethoxy group when p=1 or a hydroxyl group or —NQ$_2$ group, in which each Q is lower alkyl, when p=0, Z represents a hydrogen atom, a monovalent hydrocarbon group or a monovalent halogenated hydrocarbon group, a is 0, 1 or 2, b is 0, 1, 2 or 3, n is 0 or 1 and p is 0 or 1.

2. Organosilicon compounds as claimed in claim 1 wherein p=1 and X represents the methoxy group or the ethoxy group.

3. Organosilicon compounds as claimed in claim 1 wherein p is 0 and X represents the —NQ$_2$ group.

4. Siloxanes as claimed in claim 1 wherein at least 70 percent of the total R' and Z substituents are methyl groups.

5. A process for the preparation of organosilicon compounds as defined in claim 1 which consists essentially of reacting together (A) a compound represented by the general formula

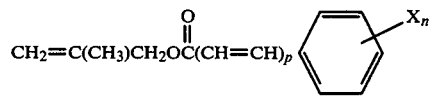

X represents a hydroxyl, methoxy or ethoxy group when p=1 or a hydroxyl group or —NQ$_2$ group, wherein Q is lower alkyl, when p=1, p is 0 or 1 and n is 0 or 1, and (B) an organosilicon compound which is a silane represented by the general formula

or a siloxane having in the molecule at least one unit of the general formula

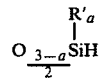

any other units present in the siloxane being those represented by the general formula

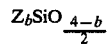

wherein R', Z, a and b are as defined in claim 1.

6. A process as claimed in claim 5 wherein p=1 and X represents the methoxy group or the ethoxy group.

7. A process as claimed in claim 5 wherein p=0 and X represents the —NQ$_2$ group.

8. A process as claimed in claim 5 wherein there is present as a catalyst for the reaction a compound or a complex of a platinum metal.

9. A sunscreen composition which contains a carrier and an effective amount of an organosilicon compound as claimed in claim 1.

* * * * *